United States Patent [19]
Itoh et al.

[11] Patent Number: 5,948,936
[45] Date of Patent: Sep. 7, 1999

[54] METHOD FOR PRODUCTION OF SULFIDE GROUP-CONTAINING THIOL COMPOUND

[75] Inventors: Hirokazu Itoh, Hyogo; Kazuaki Abe; Takashi Tomita, both of Osaka, all of Japan

[73] Assignees: Nippon Shokubai Co. Ltd., Japan; Elf Atochem S.A., France

[21] Appl. No.: 08/892,292

[22] Filed: Jul. 14, 1997

[30] Foreign Application Priority Data

Jul. 16, 1996 [JP] Japan ................................ 8-186372
Jul. 16, 1996 [JP] Japan ................................ 8-186373
Jul. 16, 1996 [JP] Japan ................................ 8-186374

[51] Int. Cl.$^6$ ................................................. C07C 321/02
[52] U.S. Cl. ........................... 560/152; 568/63; 568/41; 528/66
[58] Field of Search .................... 568/39, 38, 41, 568/59, 57, 63, 66, 67, 51; 560/152

[56] References Cited

U.S. PATENT DOCUMENTS 2,490,984  12/1949  Snyder .
2,497,100   2/1950  Snyder .
4,163,832   8/1979  Oswald ....................................... 528/76

FOREIGN PATENT DOCUMENTS 696774  9/1940  Germany .
7-5585  1/1995  Japan .

OTHER PUBLICATIONS

CA:114:135867, Abs of "Synthesis and pharmacological properties of N–[3–{3–(1piperidinyllmethyl)phenoxy}propyl]–2–(2–hydroxyethylthio) acetamide and related compounds as anti-ulcer agents", Chem Pharm Bull (1990) 38(11), pp. 3035–3041.

European Search Report, May 14, 1998.
Fokin et al., "Reaction For Nucleophilic Opening of Thiirane Ring by Thiols", *Bulletin Acad. Sci. of USSR, Div. Chem. Sci.*, 24:582–584, 1975.
Culvenor et al., The Preparation and Reactions of Aliphatic and Alicyclic Ethylene Sulphides, J. Chem. Soc., 1949, pp. 282–287.
Fokin et al., Reaction for Nucleophilic Opening of Thiirane Ring by Thiols, Izvestiya Akademii Nauk SSSR, 1974, pp. 582–584.
Leong et al., Some Addition Reactions of Pentafluorothiophenol and Pentafluorobenzenesul fenyl Chloride, Journal of Flourine Chemistry, 1975, pp. 145–159.
MacKillop et al., Reactive Liquid Polymers of Propylene Sulphide, European Polymer Journal, 1971, vol. 7, pp. 189–201.
Reaction of β–Propiolactone with Ethylene Glycol and Ethane Diol, Jap. Chem. Journ., 1960, vol. 81, pp. 328–331 (partial translation attached).
Meade et al., Some Reactions of Ethylene Sulphide and a New Method of Preparation of Vicinal Dithiols, J. Chem. Soc., 1948, pp. 1894–1895.
Snyder et al., Synthesis of Mercaptans from Olefin Sulfides, J.A.C.S., 69, 1947, pp. 2675–2677.

*Primary Examiner*—Gary Geist
*Assistant Examiner*—Jean F. Vollano
*Attorney, Agent, or Firm*—Fish & Richardson P.C.

[57] ABSTRACT

A method for the production of a sulfide group-containing thiol compound which comprises causing alkylene sulfide to react with a thiol compound in the presence of at least one basic catalyst selected from the group consisting of basic ion-exchange resins, quaternary ammonium compounds and alkyl pyridinium compounds, thereby inducing the ring-opening addition of the alkylene sulfide to the thiol compound. Further, a method for the production of a sulfide group-containing mercaptocarboxylic ester which comprises causing an alkylene sulfide to react with a mercaptocarboxylic ester.

5 Claims, No Drawings

METHOD FOR PRODUCTION OF SULFIDE GROUP-CONTAINING THIOL COMPOUND

BACKGROUND OF THE INVENTION

1. Field of the Invention

This invention relates to a method for the production of a sulfide group-containing thiol compound. More particularly, this invention relates to a method for the production of a sulfide group-containing thiol compound by the ring-opening addition of alkylene sulfide to a thiol compound.

The sulfide group-containing thiol compounds which are obtained by the method of this invention are useful compounds which find extensive utility such as in chelating agents, lubricant additives, additives for rubber, additives for refined petroleum oils, and polymerization chain transfer agents.

2. Description of the Prior Art

As means for producing a sulfide group-containing thiol compound by the ring-opening addition of alkylene sulfide to a thiol compound, a method which effects the reaction in the absence of a catalyst has been heretofore disclosed in DE-A-696, 774. Since this method requires a high temperature, however, U.S. Pat. No. 2,490,984 has proposed a method which uses boron trifluoride as a catalyst for the reaction and U.S. Pat. No. 2,497,100 a method which uses sodium alkoxide by way of improvement. Methods which similarly use alkali metal alkoxides have been also proposed in J. Am. Chem. Soc. (1947), Vol. 69, page 2675–2677, J. Chem. Soc. (1948), page 1894–1895, and J. Chem. Soc. (1949), page 282–287. Though these catalysts are highly active, they are at a disadvantage in manifesting low selectivity for the products aimed at because they are liable, when taking part in a reaction using ethylene sulfide, to induce the polymerization of ethylene sulfide.

A case of study using triethyl amine as a catalyst has been reported in Izv. Akad. Nauk, SSSR, Ser. Khim. (1975), No. 3, page 660–662. Then, U.S. Pat. No. 4,163,832 discloses a method which similarly uses either such amine compounds as trimethyl amine and triethyl amine or trimethyl phosphine. Further, J. Fluorine Chem. (1975), Vol. 6, page 145–159 discloses a reaction of pentafluorothiophenol with ethylene sulfide by the use of pyridine. When amine compounds and pyridines are used as a catalyst, they indeed go to improve the selectivity for a relevant reaction. When the reaction involves a thiol compound with low reactivity or alkylene sulfide other than ethylene sulfide, however, this catalyst is at a disadvantage in lowering the reaction velocity. Moreover, since the thiol compound is weakly acidic, the basic amine catalyst which exists in the system poses the problem that it is not thoroughly separated and removed with ease even by the distillation.

JP-B-07-5,585 has disclosed a method for effecting the reaction in a sodium hydroxide-benzene type aqueous solution with benzyl trimethyl ammonium chloride as a catalyst. This method, however, is deficient in yield and selectivity. The use of this quaternary ammonium compound as a catalyst is at a disadvantage in easily inducing the polymerization of alkylene sulfide due to the presence of water in a two-phase system and in not being applicable to a thiol compound containing an easily hydrolyzable ester group.

As means for producing a sulfide group-containing mercaptocarboxylic ester, Chem. Pharm. Bull., 38(11), pp. 3035–3041 (1990) has disclosed a method for implementing the production by causing ethane-1,2-dithiol to react with chloroacetic ester in the presence of triethyl amine. This method, however, is deficient in economic usefulness because it gives rise to a by-product containing halogen. Japan Chemical Journal, Vol. 81, pp. 328–331 (1960) teaches to obtain an ester by causing ethanol to react with the reaction product of β-propiolactone with ethane-1,2-dithiol. This method forms by-products copiously and suffers a poor yield. Eur. Polym. J., 7, pp. 189–201 (1971) reports a method for polymerizing propylene sulfide by using mercaptopropionic acid as a chain transfer agent. The product obtained by this reaction is a polymer. This reaction has been incapable of obtaining such a low adduct as with the number of mols of added alkylene sulfide in the approximate range of 1 to 3.

It is, therefore, an object of this invention to provide a novel method for the production of a sulfide-containing thiol compound.

Another object of this invention is to provide a method for the production of a sulfide group-containing thiol compound by the use of a catalyst which can manifest high activity fit for various thiol compounds, avoid inducing the polymerization of alkylene sulfide, and promote the ring-opening addition reaction with high selectivity.

Further object of this invention is to provide a novel method for the production of a sulfide group-containing mercaptocarboxylic ester.

Furthermore object of this invention is to provide a method for the production of a sulfide group-containing mercaptocarboxylic ester by the use of a catalyst capable of proceeding the reaction by the ring-opening addition with high selectivity without inducing the polymerization of an alkylene sulfide.

SUMMARY OF THE INVENTION

These objects can be attained by the following items (1) to (17).

(1) A method for the production of a sulfide group-containing thiol compound, characterized by causing alkylene sulfide represented by the general formula (2):

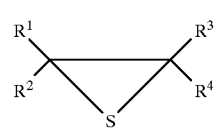

(2)

(wherein $R^1$, $R^2$, $R^3$, and $R^4$, which may be the same or different, each represents a hydrogen atom, an alkyl group of 1 to 10 carbon atoms, or an aromatic group of 6 to 15 carbon atoms) to react with a thiol compound in the presence of at least one basic catalyst selected from the group consisting of basic ion-exchange resins, and quaternary ammonium compounds and alkyl pyridinium compounds both represented by the general formula (1):

A⁺B⁻ (1)

(wherein A stands for quaternary ammonium or alkyl pyridinium, B for RCOO, ROCOO, RO, RS, or NCS, provided that R stand for a hydrogen atom, an alkyl group of 1 to 18 carbon atoms, or an aromatic group of 6 to 18 carbon atoms), thereby inducing the ring-opening addition of the alkylene sulfide to the thiol compound.

(2) A method according to (1) mentioned above, wherein the basic ion-exchange resin is at least one ion-exchange resin selected from the group consisting of resins having a tertiary amino group, resins having a quaternary ammonium group, and resins having a pyridine ring severally as a functional group.

(3) A method according to (1) mentioned above, wherein the quaternary ammonium compound is a compound represented by the general formula (3):

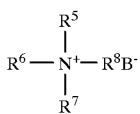

(wherein $R^5$, $R^6$, $R^7$, and $R^8$, which may be identical or different, each represents an alkyl group of 1 to 20 carbon atoms, an aromatic group of 6 to 20 carbon atoms, a benzyl group, or an allyl group and B has the same meaning as defined above).

(4) A method according to (1) mentioned above, wherein the alkyl pyridinium compound is a compound represented by the general formula (4):

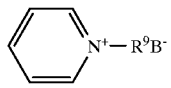

(wherein $R^9$ stands for an alkyl group of 1 to 20 carbon atoms and B has the same meaning as defined above).

(5) A method according to (3) or (4) mentioned above, wherein the reaction is carried out in a non-aqueous system.

(6) A method according to (1) mentioned above, wherein the reaction is carried out by sequentially adding the alkylene sulfide into the reaction system.

(7) A method according to any of (1) to (6) mentioned above, wherein the thiol compound is one member selected from the group consisting of polythiols, mercaptoalkanoic esters, allyl mercaptan, furfuryl mercaptan, and compounds represented by the general formula (5):

[wherein $R^{10}$ stands for a hydrogen atom, an alkyl group of 1 to 20 carbon atoms, a hydroxyalkyl group of 2 to 20 carbon atoms, an aromatic group of 6 to 20 carbon atoms, or $R^{11}$CO— (wherein $R^{11}$ stands for an alkyl group of 1 to 20 carbon atoms or an aromatic group of 6 to 20 carbon atoms)].

(8) A method according to any of (1) to (7) mentioned above, wherein the thiol compound is a compound represented by the general formula (5):

[wherein $R^{10}$ stands for a hydrogen atom, an alkyl group of 1 to 20 carbon atoms, a hydroxyalkyl group of 2 to 20 carbon atoms, an aromatic group of 6 to 20 carbon atoms, or $R^{11}$CO— (wherein $R^{11}$ stands for an alkyl group of 1 to 20 carbon atoms or an aromatic group of 6 to 20 carbon atoms)].

(9) A method according to any of (1) to (7) mentioned above, wherein the alkylene sulfide is ethylene sulfide or propylene sulfide and the thiol compound is one member selected from the group consisting of mercaptoalkanoic esters, mercaptoalkanols, aromatic thiols, aromatic thiocarboxylic acids, and alkane thiols.

(10) A method according to (9) mentioned above, wherein the thiol compound is one member selected from the group consisting of mercaptoalkanoic esters and mercaptoalkanols.

(11) A method according to (1) mentioned above, wherein the amount of the basic catalyst used is in the range of 0.01 to 10 parts by weight, based on 100 parts by weight of the reaction mixture.

(12) A method according to (1) mentioned above, wherein the amount of the thiol compound is in the range of 1 to 10 mols per mol of the alkylene sulfide.

(13) A method according to (1) mentioned above, wherein the reaction is carried out at a temperature in the range of 0° to 200° C.

(14) A method for the production of a sulfide group-containing mercaptocarboxylic ester represented by the general formula (7):

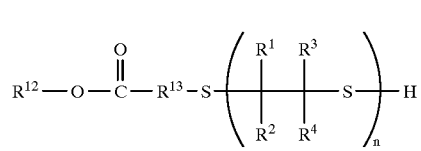

(wherein $R^1$, $R^2$, $R^3$, and $R^4$, which maybe identical or different, each represents a hydrogen atom, an alkyl group of 1 to 10 carbon atoms, or an aromatic group of 6 to 15 carbon atoms, $R^{12}$ for a hydrocarbon group of 1 to 20 carbon atoms, and $R^{13}$ for an alkylene group of 1 to 3 carbon atoms, and n is an integer in the range of 1 to 3), characterized by causing an alkylene sulfide represented by the general formula (2):

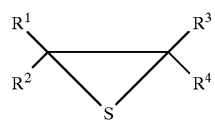

(wherein $R^1$, $R^2$, $R^3$, and $R^4$ have the same meanings as defined above) to react with a mercaptocarboxylic ester represented by the general formula (6):

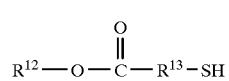

(wherein $R^{12}$ and $R^{13}$ have the same meanings as defined above).

(15) A method according to (14) mentioned above, wherein the reaction is carried out in the presence of a basic catalyst or a phosphine catalyst.

(16) A method according to (14) or (15) mentioned above, wherein the amount of the mercaptocarboxylic ester is in the range of 1 to 10 mols per mol of the alkylene sulfide.

(17) A method according to any of (14) to (16) mentioned above, wherein the reaction is carried out by the sequential addition of the alkylene sulfide into the reaction system.

(18) A method according to any of (14) to (17) mentioned above, wherein the alkylene sulfide is ethylene sulfide or propylene sulfide and the mercaptocarboxylic ester is 3-mercaptopropionic ester or 2-mercaptoacetic ester.

This invention allows a sulfide group-containing thiol compound to be produced with high activity and high selectivity by the ring-opening addition of alkylene sulfide to a thiol compound. Since the catalyst for this invention contains no halogens, it perfectly fits for the commercial production of the sulfide group-containing thiol compound without entraining such problems as corrosion of an equipment. Since the basic ion-exchange resin, when used as a catalyst, is in a solid state, the recovery and removal of the catalyst from the reaction mixture can be obtained very easily. Further, this invention allows a sulfide group-containing mercaptocarboxylic ester to be produced with a high yield from an alkylene sulfide and a mercaptocarboxylic ester as raw materials without substantially forming by-products which are subsequently discarded.

DESCRIPTION OF THE PREFERRED EMBODIMENTS

One characteristic of this invention is that a basic ion-exchange resin or a compound represented by the general formula (1):

  (1)

is used as a catalyst in the reaction for producing a sulfide group-containing thiol compound by the ring-opening addition of alkylene sulfide to a thiol compound. In this general formula, A stands for quaternary ammonium or alkyl pyridinium and B stands for RCOO, ROCOO, RO, RS, or NCS, provided that R stand for a hydrogen atom, an alkyl group of 1 to 18, preferably 1 to 8, carbon atoms, or an aromatic group of 6 to 18, preferably 6 to 10, carbon atoms. Most preferably B stands for RCOO or RO.

The basic ion-exchange resins which are usable for the catalyst include ion-exchange resins having a tertiary amino group, ion-exchange resins having a quaternary ammonium group, and ion-exchange resins having a pyridine ring severally as a functional group, which can be easily obtained generally as commercial products. Among other basic ion-exchange resins cited above, weakly basic ion-exchange resins having a tertiary amino group as a functional group particularly excel in both activity and selectivity and find favorable acceptance.

As respect such basic ion-exchange resins as are available in the market, the ion-exchange resins having a tertiary amino group include Amberlyst A-21, Amberlite IRA-93, Amberlite IRA-94, and Amberlite IRA-68 (produced by Rohm and Haas Company), Duolite A-368, Duolite A-561, and Duolite A-375 (produced by Duolite International Corp.), Dowex MWA-1 (produced by The Dow Chemical Company), and Diaion WA30 (produced by Mitsubishi Chemical Co., Ltd.), for example.

The ion-exchange resins having a quaternary ammonium group include Amberlite IRA-904, Amberlite IRA-938, Amberlite IRA-958, and Amberlite IRA-900 (produced by Rohm and Haas Company), Duolite A-161, Duolite A-165, and Duolite A-147 (produced by Duolite International Corp.), Dowex MSA-1 and Dowex SBR (produced by The Dow Chemical Company), and Diaion SA10A and Diaion PA306 (produced by Mitsubishi Chemical Co., Ltd.), for example.

The ion-exchange resins having a pyridine ring include Sumichelate CR-2 (produced by Sumitomo Chemical Co., Ltd.), for example.

Among these compounds, compounds represented by the general formula (3):

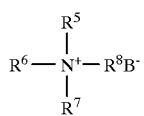  (3)

are used advantageously as the quaternary ammonium compound. In this general formula, $R^5$, $R^6$, $R^7$, and $R^8$, which may be identical or different, each represents an alkyl group of 1 to 20, preferably 1 to 18, carbon atoms, an aromatic group of 6 to 20, preferably 6 to 10, carbon atoms, a benzyl group, or an allyl group and B has the same meaning as defined above. Compounds represented by the general formula (4):

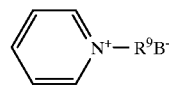  (4)

are advantageously used as the alkyl pyridinium compound. In this general formula, $R^9$ represents an alkyl group of 1 to 20, preferably 1 to 18, and most preferably 1 to 16, carbon atoms and B has the same meaning as defined above.

The typical quaternary ammonium compounds have a cation moiety which is selected among tetramethyl ammonium, tetraethyl ammonium, tetrapropyl ammonium, tetrabutyl ammonium, tetrahexyl ammonium, tetraoctyl ammonium, benzyltrimethyl ammonium, benzyltriethyl ammonium, phenyltrimethyl ammonium, phenyltriethyl ammonium, cetyl benzyldimethyl ammonium, and hexadecyl trimethyl ammonium, and an anion moiety which is selected among acetate, propionate, formate, benzoate, methyl carbonate, ethyl carbonate, propyl carbonate, butyl carbonate, phenyl carbonate, hydroxide, methoxide, ethoxide, propoxide, butoxide, phenoxide, hydrosulfide, methyl thiolate, ethyl thiolate, propyl thiolate, butyl thiolate, phenyl thiolate, and thiocyanate.

The typical alkyl pyridinium compounds have a cation moiety which is selected among methyl pyridinium, ethyl pyridinium, propyl pyridinium, butyl pyridinium, octyl pyridinium, decyl pyridinium, lauryl pyridinium, cetyl pyridinium, and benzyl pyridinium, and an anion moiety which is selected among acetate, propionate, formate, benzoate, methyl carbonate, ethyl carbonate, propyl carbonate, butyl carbonate, phenyl carbonate, hydroxide, methoxide, ethoxide, propoxide, butoxide, phenoxide, hydrosulfide, methyl thiolate, ethyl thiolate, propyl thiolate, butyl thiolate, phenyl thiolate, and thiocyanate.

Among these compounds, tetraalkyl ammonium acetates, benzyl trialkyl ammonium acetates, tetraalkyl ammonium hydroxides, and benzyl trialkyl ammonium hydroxides are particularly advantageous and are readily available as reagents and industrial products.

These compounds are highly active as the catalyst and capable of fulfilling the role of a catalyst in a small amount. The fact that they exhibit high activity even in a non-aqueous system deserves a special notice. Thus, they not only permit the adoption of thiol compounds possessing such easily hydrolyzable functional groups as ester groups as a raw material but also allow easy implementation of the ring-opening addition of alkylene sulfide to a mercaptoalkanoic ester. Among other alkylene sulfides, ethylene sulfide possesses particularly high reactivity and tends to induce such secondary reactions as tolymerization. Owing to the use of the catalyst according to this invention, ethylene sulfide is prevented from inducing such secondary reactions and enabled to produce a sulfide group-containing thiol compound aimed at with high selectivity. Further even from the commercial point of view, the catalyst which contains no halogen is actually highly advantageous because it is free from such problems as corrosion of an equipment.

Though the amount of this catalyst to be used in effecting the reaction is not particularly limited, it is generally in the range of 0.01 to 10 parts by weight, preferably 0.05 to 1 part by weight, based on 100 parts by weight of the reaction mixture. If this amount is less than 0.01 part by weight, the reaction velocity will be unduly low. Conversely, if this amount exceeds 10 parts by weight, the excess will go to impair the economy of the reaction, though it will have no adverse effect on the reaction itself. The method for using this catalyst varies with the form of the reaction. The catalyst may be added to the reaction mixture at the initial stage of the reaction or may be added sequentially thereto. The catalyst may be used in the form of a single compound or a mixture of two or more compounds.

The manner of using the basic ion-exchange resin catalyst varies with the form of reaction. For the reaction which is performed batchwise, the catalyst may be added at the outset of the reaction or may be successively added. Since this catalyst is in a solid state, it can be very easily separated and recovered after the reaction by such means as decantation or filtration. In the reaction which is performed continuously, the catalyst may be retained in the form of a fixed bed in the reaction vessel and consequently enabled to permit continuous passage therethrough of the reaction mixture.

The alkylene sulfide to be used in this invention is a compound represented by the general formula (2).

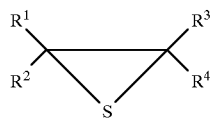

(2)

In this formula, $R^1$, $R^2$, $R^3$, and $R^4$, which may be the same or different, each represents a hydrogen atom, an alkyl group of 1 to 10, preferably 1 to 6, carbon atoms, or an aromatic group of 6 to 15, preferably 6 to 10, carbon atoms. As typical examples of the alkylene sulfide, ethylene sulfide, propylene sulfide, isobutylene sulfide, and styrene sulfide may be cited. Among other alkylene sulfides cited above, ethylene sulfide and propylene sulfide prove particularly appropriate.

As the thiol compound which may be used in this invention, polythiols, mercaptoalkanoic esters, allyl mercaptan, furfuryl mercaptan, and compounds represented by the general formula (5) as following:

may be cited. Among other thiol compounds cited above, mercaptoalkanoic esters and compounds represented by the general formula (5), more preferably, mercaptoalkanoic esters, mercaptoalkanols, aromatic thiols, aromatic thiocarboxylic acids, and alkane thiols, particularly mercaptoalkanoic esters and mercaptoalkanols may be preferably used. In this formula, $R^{10}$ stands for a hydrogen atom, an alkyl group of 1 to 20, preferably 1 to 12, carbon atoms, a hydroxyalkyl group of 2 to 20, preferably 2 to 8, carbon atoms, an aromatic group of 6 to 20, preferably 6 to 12, carbon atoms, or $R^{11}CO-$ (wherein $R^{11}$ stands for an alkyl group of 1 to 20, preferably 1 to 8, carbon atoms or an aromatic group of 6 to 20, preferably 6 to 12, carbon atoms).

As typical examples of the thiol compound, alkane thiols such as methane thiol, ethane thiol, propane thiol, butane thiol, hexane thiol, and octane thiol, polythiols such as ethane dithiol, propane dithiol, butane dithiol, and bis(2-mercaptoethyl) sulfide, aromatic thiols such as thiophenol, 1,2-benzene dithiol, 1,4-benzene dithiol, and 4-mercaptophenol, mercaptoalkanols such as 2-mercaptoethanol, 3-mercaptopropanol, 1-methyl-2-mercaptoethanol, and thioglycerol, mercaptoalkanoic esters such as methyl ester, ethyl ester, propyl ester, butyl ester, hexyl ester, n-octyl ester, isooctyl ester, 2-ethylhexyl ester, lauryl ester, stearyl ester, ester of ethylene glycol, ester of glycerin, ester of trimethylol propane, ester of pentaerythritol, and ester of dipentaerythritol of 3-mercaptopropionic acid, methyl ester, ethyl ester, propyl ester, butyl ester, hexyl ester, n-octyl ester, isooctyl ester, 2-ethylhexyl ester, lauryl ester, stearyl ester, ester of ethylene glycol, ester of glycerin, ester of trimethylol propane, ester of pentaerythritol, and ester of dipentaerythritol of 2-mercaptoproponic acid, methyl ester, ethyl ester, propyl ester, butyl ester, hexyl ester, n-octyl ester, isooctyl ester, 2-ethylhexyl ester, lauryl ester, stearyl ester, ester of ethylene glycol, ester of glycerin, ester of trimethylol propane, ester of pentaerythritol, and ester of dipentaerythritol of thioglycolic acid, thiocarboxylic acids such as thioacetic acid, thiopropionic acid, thiobutyric acid, and thiobenzoic acid, and allyl mercaptan, benzyl mercaptan, furfuryl mercaptan, and hydrogen sulfide may be cited.

In the ring-opening addition of alkylene sulfide to a thiol compound according to this invention, the number of mols of the alkylene sulfide to be added in the product can be controlled by the ratios of the raw materials to be charged. The production of an one mol adduct can be attained generally by using the thiol compound in an excess amount. To be specific, the thiol compound is used in an amount in the range of 1 to 10 mols, preferably 1 to 5 mols, per mol of the alkylene sulfide. If the thiol compound is used in an excess amount, the excess will have no adverse effect on the reaction but will impair the productivity. When the thiol compound to be used has high reactivity such that the acid dissociation constant, pKa, is smaller than 8.0, the one mol adduct can be preferentially obtained even at a charging ratio (molar ratio) of 1:1.

In the batchwise reaction, the selectivity for the one mol adduct is higher when the alkylene sulfide is successively added to the reaction system than when the raw materials are added collectively to the reaction system. When the alkylene sulfide is used in an excess amount, though the number of mols of addition is larger than 1, the product more often than not has a width of distribution. In this case, the amount of the alkylene sulfide to be used is generally in the range of 1 to 10 mols, preferably in the range of 1 to 3 mols, per mol of the thiol compound. If the alkylene sulfide is used in a still larger excess, the control of the number of mols of addition will become difficult.

The reaction temperature in the method of this invention is generally in the range of 0° to 200° C., preferably in the range of 10° to 150° C. The reaction contemplated by this invention proceeds amply even at or below room temperature because the basic ion-exchange resin as the catalyst to be used in this method is highly active. Though the reaction pressure is not particularly limited, it is generally in the range of 1 to 100 kg/cm², preferably in the range of 1 to 20 kg/cm². For the purpose of preventing the thiol group from being oxidized with oxygen during the course of the reaction, it is appropriate to keep the interior of the reaction system under an ambience of an inert gas. As the inert gas, nitrogen, argon, or helium may be used.

The method of this invention, when necessary, permits the use of a solvent. When the reaction elects to use a solvent, though the concentration of the reaction mixture is not particularly limited, it is generally in the range of 5 to 90% by weight, preferably in the range of 20 to 60% by weight. If this concentration is less than 5% by weight, the reaction velocity will be unduly low and, at the same time, the isolation of the product will prove uneconomical because the amount of the solvent to be separated and recovered is unduly large. Conversely, if this amount exceeds 90% by weight, the effect of diluting the reaction mixture with the solvent will not be manifested sufficiently.

The solvent to be used in the method of this invention may be selected among solvents that are inert to the thiol compound and the alkylene sulfide. As typical examples of the solvent usable effectively herein, hydrocarbon type solvents such as hexane, cyclohexane, pentane, benzene, toluene, xylene, p-cymene, and mesitylene, ether type solvents such as diethyl ether, dibutyl ether, tetrahydrofuran, dioxane, 1,2-dimethoxy ethane, and diethylene glycol dimethyl ether, ketone type solvents such as acetone, methylethyl ketone, and methylisobutyl ketone, amide type solvents such as N,N-dimethyl formamide, N,N-dimethyl acetamide, formamide, and N-methylpyrrolidone, and acetonitrile, nitromethane, chlorobenzene, dimethyl sulfoxide, hexamethyl phosphoric triamide, and 1,3-dimethyl-2-imidazolidinone may be cited. The removal of the heat of reaction can be more easily attained by performing the reaction under the reflux of the solvent.

By performing the reaction as described above, a sulfide group-containing thiol compound represented by the following general formula (8):

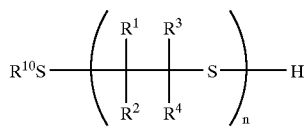

(8)

(wherein $R^1$, $R^2$, $R^3$, $R^4$, and $R^{10}$ have the same meanings as defined above and n is an integer in the range of 1 to 6, preferably in the range of 1 to 3), can be obtained.

Another characteristic of this invention is that a sulfide group-containing mercaptocarboxylic ester can be obtained by causing a mercaptocarboxylic ester to react with an alkylene sulfide. To obtain a sulfide group-containing mercaptocarboxylic ester having the number of mols of added alkylene sulfide controlled in the range of 1 to 3, the amount of the mercaptopropionic ester to be used per mol of the alkylene sulfide advantageously is in the range of 1 to 10 mols. If the amount of the mercaptocarboxylic ester to be used is less than 1 mol per mol of the alkylene sulfide, the number of mols of the added alkylene sulfide will possibly increase and the reaction will form a compound close to a polymer from the physical point of view. Conversely, if this amount exceeds 10 mols, the excess will go to lower the productivity, though a sulfide group-containing mercaptocarboxylic ester aimed at will be formed.

The reactivity of the mercaptocarboxylic ester is variable with the kind of the ester to be used. Specifically, for the purpose of obtaining an one-mol adduct of alkylene sulfide, a 3-mercaptopropionic ester, for example, is appropriately used in an amount in the range of 3 to 7 mols and a 2-mercaptoacetic ester, a compound having higher reactivity, in an amount in the range of 1 to 2 mols, per mol of the alkylene sulfide.

By causing the alkylene sulfide to be sequentially added into the reaction system, the possible increase in the number of mols of addition can be controlled more effectively.

The mercaptocarboxylic ester which is used in an excess amount in this reaction can be easily separated and recovered as by distillation after the reaction and can be reused by the circulation.

The alkylene sulfide to be used in this invention is a compound represented by the general formula (2):

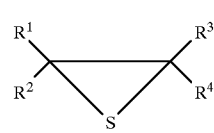

(2)

In this general formula, $R^1$, $R^2$, $R^3$, and $R^4$ have the same meanings as defined above. As typical examples thereof, ethylene sulfide, propylene sulfide, isobutylene sulfide, and styrene sulfide may be cited Among other alkylene sulfides mentioned above, ethylene sulfide and propylene sulfide prove particularly appropriate.

The mercaptocarboxylic ester to be used in this invention is a compound represented by the general formula (6):

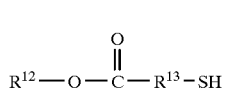

(6)

In this general formula, $R^{12}$ stands for a hydrocarbon group of 1 to 20 carbon atoms and preferably an alkyl group of 1 to 15 carbon atoms, and $R^{13}$ for an alkylene group of 1 to 3, preferably 1 to 2, carbon atoms. As typical examples of this mercaptocarboxylic ester, 3-mercaptopropionic esters such as methyl 3-mercaptopropionate, ethyl 3-mercaptopropionate, propyl 3-mercaptopropionate, butyl 3-mercaptopropionate, n-octyl 3-mercaptopropionate, 2-ethylhexyl 3-mercaptopropionate, and n-dodecyl 3-mercaptopropionate, 2-mercaptopropionic esters such as methyl 2-mercaptopropionate, ethyl 2-mercaptopropionate, propyl 2-mercaptopropionate, butyl 2-mercaptopropionate, n-octyl 2-mercaptopropionate, 2-ethylhexyl 2-mercaptopropionate, and n-dodecyl 2-mercaptopropionate, and 2-mercaptoacetic esters such as methyl 2-mercaptoacetate, ethyl 2-mercaptoacetate, propyl 2-mercaptoacetate, butyl 2-mercaptoacetate, n-octyl 2-mercaptoacetate, 2-ethylhexyl 2-mercaptoacetate, and n-dodecyl 2-mercaptopropionate may be cited. Among other mercaptocarboxylic esters enumerated above, 3-mercaptopropionic esters and 2-mercaptoacetic esters prove advantageous.

In the method of this invention, the reaction can be proceeded smoothly in the presence of a basic catalyst or a phosphine catalyst. As concrete examples of the basic catalyst, alkali metal hydroxides such as sodium hydroxide, potassium hydroxide, and lithium hydroxide, alkaline earth metal hydroxides such as magnesium hydroxide, calcium hydroxide, and barium hydroxide, alkaline earth metal oxides such as magnesium oxide, calcium oxide, and barium oxide, alkali metal alkoxides such as sodium methoxide, sodium ethoxide, sodium isopropoxide, sodium butoxide, sodium phenoxide, potassium methoxide, potassium ethoxide, potassium isopropoxide, potassium butoxide, and potassium phenoxide, alkyl tertiary amines such as trimethyl amine, triethyl amine, triisopropyl amine, tributyl amine, and N-ethyldiisopropyl amine, alkylene polyamines such as N,N,N',N'-tetramethylethylene diamine, N,N,N',N'-tetramethyl-1,3-diamino propane, N,N,N',N'-tetramethyl-1,4-diamino butane, N,N,N',N'-tetramethyl-1,6-diamino hexane, and N,N,N',N',N'-pentamethyl diethylene triamine, amines such as N-methyl morpholine, 1,4-dimethyl piperazine, 2,4,6-tris(dimethylaminomethyl) phenol, 1,4-diazabicyclo[2.2.2]octane, and 1,8-diazabicyclo[5.4.0] undecene, nitrogen-containing heterocyclic compounds such as pyridine, picoline, lutidine, quinoline, pyrazine, 4-dimethylamino pyridine, and 1-methyl imidazole, compounds selected among such tetraalkyl quaternary ammonium compounds as tetramethyl ammonium compounds, tetraethyl ammonium compounds, tetrapropyl ammonium compounds, tetrabutyl ammonium compounds, benzyl trimethyl ammonium compounds, benzyl triethyl ammonium compounds, and cetyl trimethyl ammonium compounds, which a pair anions are selected among carboxylates, alcoholates, thiolates, hydroxides, and hydrosulfides, compounds selected among such compounds selected among such alkyl pyridinium compounds as methyl pyridinium compounds, ethyl pyridinium compounds, propyl pyridinium compounds, butyl pyridinium compounds, cetyl pyridinium compounds, and benzyl pyridinium compounds, which pair anions are selected among carboxylates, alcoholates, thiolates, hydroxides, and hydrosulfides, and basic ion-exchange resins having a tertiary amino group or a quaternary ammonium group as a functional group may be cited. As concrete examples of the phosphine catalyst, trimethyl phosphine, triethyl phosphine, tripropyl phosphine, tributyl phosphine, and triphenyl phosphine may be cited.

Though the amount of the basic catalyst or phosphine catalyst to be used is not particularly limited, it is generally in the range of 0.01 to 10 parts by weight, referably 0.05 to 1 part by weight, based on 100 parts by weight of the reaction mixture. If this amount is less than 0.01 part by weight, the reaction velocity will be unduly low. Conversely, if this amount exceeds 10 parts by weight, the excess will go to impair the economy of the reaction, though it will have no adverse effect on the reaction itself.

The reaction temperature in the method of this invention is generally in the range of 0° to 200° C., preferably 10° to 150° C. Though the reaction pressure is not particularly limited, it is generally in the range of 1 to 100 kg/cm$^2$, preferably 1 to 20 kg/cm$^2$. For the purpose of precluding the otherwise possible oxidation of the mercapto group with oxygen during the course of reaction, it is advantageous to retain the interior of the reaction system under an ambience of an inert gas. As the inert gas, nitrogen, argon, helium, etc. may be used.

The method of this invention, when necessary, may use a solvent. When a solvent is used, the concentration of the reaction mixture is not particularly limited, but is generally in the range of 5 to 90% by weight, preferably 20 to 60% by weight. If this concentration is less than 5% by weight, the reaction velocity will be unduly low and, at the same time, the isolation of the reaction product will necessitate the separation and recovery of a large amount of the solvent possibly to the extent of impairing the economy of the reaction. Conversely, if the amount exceeds 90% by weight, the effect of diluting the reaction mixture with the solvent will not be manifested satisfactorily.

Any solvents which are inert to the mercaptocarboxylic ester and the alkylene sulfide are invariably usable effectively in the method of this invention. As typical examples of the solvent, hydrocarbon type solvents such as hexane, cyclohexane, pentane, benzene, toluene, xylene, p-cymene, and mesitylene, ether type solvents such as diethyl ether, dibutyl ether, tetrahydrofuran, dioxane, 1,2-dimethoxy ethane, and diethylene glycol dimethyl ether, ketone type solvents such as acetone, methylethyl ketone, and methyl isobutyl ketone, amide type solvents such as N,N-dimethyl formamide, N,N-dimethyl acetamide, formamide, and N-methyl pyrrolidone, and acetonitrile, nitromethane, chlorobenzene, dimethyl sulfoxide, hexamethyl phosphoric triamide, and 1,3-dimethyl-2-imidazolidinone may be cited. When the alkylene sulfide is other than ethylene sulfide, such alcohols as methanol, ethanol, propanol, butanol, 2-methoxy ethanol, 2-ethoxy ethanol, and 2-butoxy ethanol are further usable as the solvent. The heat of reaction can be removed more easily by carrying out the reaction under the reflux of the solvent.

By carrying out the reaction as described above, the sulfide group-containing mercaptocarboxylic ester represented by the general formula (7):

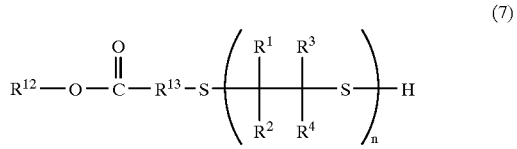

(7)

(wherein $R^1$, $R^2$, $R^3$, $R^4$, $R^{12}$, and $R^{13}$ have the same meanings as defined above and n is an integer in the range of 1 to 3, preferably 1 to 2) can be obtained.

Now, this invention will be described more specifically below with reference to working examples and controls. It should be noted, however, that this invention is not limited by these examples.

EXAMPLE 1

In a four-neck flask provided with a stirrer, a reflux condenser, a thermometer, and a dropping funnel, 24.0 g (200 m.mols) of methyl 3-mercaptopropionate, 40 g of toluene, and 0.4 g of a basic ion-exchange resin (produced by Rohm and Haas Company and marketed under trademark designation of "Amberlyst A-21") were placed and kept at a temperature of 50° C. under a stream of nitrogen and 2.4 g (40 m.mols) of ethylene sulfide was added dropwise thereto over a period of 30 minutes. After the ensuant reaction was continued at the same temperature for two hours, the reaction product was extracted from the flask and analyzed by gas chromatography. Consequently, it was found to consist of one-mol adduct and two-mol adduct of ethylene sulfide at a ratio of 89:11 (area ratio of gas chromatograph). Thus, the total yield of the obtained ethylene sulfide adducts was found to be 98%, based on the weight of the ethylene sulfide. The results are shown in Table 1 and Table 2.

EXAMPLE 2

The results shown in Table 1 and Table 2 were obtained by following the procedure of Example 1 while using 24.0 g (200 m.mols) of ethyl 2-mercaptoacetate and 12.0 g (200 m.mols) of ethylene sulfide as the raw materials for the reaction.

EXAMPLE 3

The results shown in Table 1 and Table 2 were obtained by following the procedure of Example 1 while using 15.6 g (200 m.mols) of 2-mercaptoethanol and 2.4 g (40 m.mols) of ethylene sulfide as the raw materials for the reaction.

EXAMPLE 4

The results shown in Table 1 and Table 2 were obtained by following the procedure of Example 1 while using 27.6 g (200 m.mols) of thiobenzoic acid and 12.0 g (200 m.mols) of ethylene sulfide as the raw materials for the reaction.

EXAMPLE 5

The results shown in Table 1 and Table 2 were obtained by following the procedure of Example 1 while using 22.0 g (200 m.mols) of thiophenol and 2.4 g (40 m.mols) of ethylene sulfide as the raw materials for the reaction.

nitrogen and 6.0 g (100 m.mols) of ethylene sulfide was added dropwise thereto over a period of 30 minutes. After the ensuant reaction was continued at the same temperature for six hours, the reaction product was extracted and analyzed by gas chromatography. The results shown in Table 1 and Table 2 were obtained.

Control 1

The results shown in Table 1 and Table 2 were obtained by repeating the procedure of Example 1 while using 0.4 g of triethyl amine as the catalyst.

TABLE 1

| | Thiol Compound (A) | Alkylene Sulfide (B) | Molar ratio of raw materials (A)/(B) | Catalyst |
|---|---|---|---|---|
| Example 1 | Methyl 3-mercapto propionate | ES | 5/1 | Amberlyst A-21 |
| Example 2 | Ethyl 2-mercaptoacetate | ES | 1/1 | Amberlyst A-21 |
| Example 3 | 2-Mercaptoethanol | ES | 5/1 | Amberlyst A-21 |
| Example 4 | Thiobenzoic acid | ES | 1/1 | Amberlyst A-21 |
| Example 5 | Thiophenol | ES | 5/1 | Amberlyst A-21 |
| Example 6 | Propane thiol | ES | 5/1 | Amberlyst A-21 |
| Example 7 | Methyl 3-mercapto propionate | PS | 1/1 | Amberlyst A-21 |
| Example 8 | Methyl 3-mercapto propionate | ES | 5/1 | Amberlite IRA-904 |
| Example 9 | Thiobenzoic acid | ES | 1/1 | Sumichelate CR-2 |
| Control 1 | Methyl 3-mercapto propionate | ES | 5/1 | Triethyl amine |

Abbreviation:
ES: Ethylene sulfide
PS: Propylene sulfide
Amberlyst A-21: Ion-exchange resin having a tertiary amino group as a functional group (produced by Rohm and Haas Company), and was used after washed with water and dried.
Amerlite IRA-904: Ion-exchange resin having a quaternary amino group as a functional group (produced by Rohm and Haas Company), and was used after pretreatment with an aqueous sodium hydroxide solution, washed with water and dried.
Sumichelate CR-2: Ion-exchange resin having a pyridine ring as a functional group (produced by Sumitomo Chemical Company), and was used after washed with water and dried.

EXAMPLE 6

The results shown in Table 1 and Table 2 were obtained by following the procedure of Example 1 while using 15.2 g (200 m.mols) of propanethiol and 2.4 g (40 m.mols) of ethylene sulfide as the raw materials for the reaction.

EXAMPLE 7

The results shown in Table 1 and Table 2 were obtained by following the procedure of Example 1 while using 24.0 g (200 m.mols) of methyl 3-mercapto propionate and 14.8 g (200 m.mols) of propylene sulfide as the raw materials for the reaction.

EXAMPLE 8

The results shown in Table 1 and Table 2 were obtained by following the procedure of Example 1 while using 0.4 g of a basic ion-exchange resin (produced by Rohm and Haas Company and marketed under trademark designation of "Amberlite IRA-904") as the catalyst instead.

EXAMPLE 9

In the same apparatus as used in Example 1, 13.8 g (100 m.mols) of thiobenzoic acid and 1.2 g of a catalyst (produced by Sumitomo Chemical Company and marketed under trademark designation of "Sumichelate CR-2") were placed and kept at a temperature of 60° C. under a stream of

TABLE 2

| | Total yield of product (%) | Ratio of product | | |
|---|---|---|---|---|
| | | 1 mol adduct | 2 mol adduct | 3 mol adduct |
| Example 1 | 98 | 89 | 11 | Trace amount |
| Example 2 | 98 | 99 | 1 | 0 |
| Example 3 | 97 | 93 | 7 | Trace amount |
| Example 4 | 96 | 100 | 0 | 0 |
| Example 5 | 99 | 97 | 3 | 0 |
| Example 6 | 83 | 48 | 40 | 22 |
| Example 7 | 73 | 88 | 12 | 0 |
| Example 8 | 87 | 85 | 15 | Trace amount |
| Example 9 | 82 | 97 | 3 | 0 |
| Control 1 | 3 | 47 | 53 | 0 |

EXAMPLE 10

In a four-neck flask provided with a stirrer, a reflux condenser, a thermometer, and a dropping funnel, 60.1 g (0.5 mol) of methyl 3-mercaptopropionate and 0.20 g of tetrabutyl ammonium acetate (produced by Aldrich) were placed and kept under a stream of nitrogen at a temperature of 50° C. and 6.0 g (0.1 mol) of ethylene sulfide was added dropwise thereto over a period of 30 minutes. The ensuant reaction was further continued at the same temperature for three hours. Then, the reaction product was extracted from the flask and analyzed by gas chromatography. The product was found to consist of a 1-mol adduct and a 2-mol adduct of ethylene sulfide at a ratio of 87:13 (area ratio of gas chromatograph). The total yield of the obtained ethylene sulfide adducts was 98%, based on the weight of the ethylene sulfide. The results are shown in Table 3 and Table 4.

EXAMPLE 11

The results shown in Table 3 and Table 4 were obtained by following the procedure of Example 10 while using 0.20 g of tetramethyl ammonium acetate (produced by Aldrich) as the catalyst instead.

EXAMPLE 12

The results shown in Table 3 and Table 4 were obtained by following the procedure of Example 10 while using 0.59 g of tetrabutyl ammonium benzoate (produced by Fluka) as the catalyst instead.

EXAMPLE 13

The results shown in Table 3 and Table 4 were obtained by following the procedure of Example 10 while using 0.20 g of tetrabutyl ammonium hydrosulfide (produced by Fluka) as the catalyst instead.

EXAMPLE 14

The results shown in Table 3 and Table 4 were obtained by following the procedure of Example 10 while using 0.20 g of tetrabutyl ammonium thiocyanate (produced by Tokyo Kasei Kogyo K. K.) as the catalyst instead.

EXAMPLE 15

The results shown in Table 3 and Table 4 were obtained by following the procedure of Example 10 while using 0.13 g of a methanol 40% benzyl trimethyl ammonium hydroxide solution (produced by Tokyo Kasei Kogyo K. K.) as the catalyst instead.

EXAMPLE 16

The results shown in Table 3 and Table 4 were obtained by following the procedure of Example 10 while using 0.53 g of a methanol 10% tetrabutyl ammonium hydroxide solution (produced by Tokyo Kasei Kogyo K. K.) as the catalyst instead.

EXAMPLE 17

The results shown in Table 3 and Table 4 were obtained by following the procedure of Example 10 while using 0.53 g of a methanol 10% tetramethyl ammonium hydroxide solution (produced by Tokyo Kasei Kogyo K. K.) as the catalyst instead.

EXAMPLE 18

In an agitation type autoclave, 9.0 g (0.1 mol) of dimethyl carbonate, 10.1 g (0.1 mol) of triethyl amine, and 10.0 g of methanol as a solvent were placed and left reacting therein at a reaction temperature of 115° C. under a reaction pressure of 5.0 kg/cm²G for 12 hours. The resultant reaction solution was cooled, extracted from the autoclave, and distilled under a reduced pressure to remove the unaltered materials and the solvent and to obtain 9.8 g of solid triethylmethyl ammonium methyl carbonate (in accordance with the method of JP-B-08-19, 060, with necessary modifications). The results shown in Table 3 and Table 4 were obtained by following the procedure of Example 10 while using 0.20 g of triethylmethyl ammonium methyl carbonate obtained as described above as the catalyst instead.

EXAMPLE 19

A solution of 5.56 g (0.02 mol) of tetrabutyl ammonium chloride in 49.0 g of methanol was kept stirred and 1.08 g (0.02 mol) of sodium methoxide was gradually added thereto with stirred. The ensuant reaction was further continued at room temperature for 15 hours. Then, the reaction solution was filtered to obtain tetrabutyl ammonium methoxide. The results shown in Table 3 and Table 4 were obtained by following the procedure of Example 10 while using 0.53 g of a methanol 10% tetrabutyl ammonium methoxide solution thus obtained as the catalyst instead.

EXAMPLE 20

To a solution of 7.16 g (0.02 mol) of cetyl pyridinium chloride monohydrate in 60.4 g of methanol, 1.08 g (0.02 mol) of sodium methoxide was added little by little as kept stirred. The ensuant reaction was further continued at room temperature for 15 hours. Then, the reaction solution was filtered to obtain cetyl pyridinium methoxide. The results shown in Table 3 and Table 4 were obtained by following the procedure of Example 10 while using 0.53 g of a methanol 10% cetyl pyridinium methoxide solution as the catalyst instead.

EXAMPLE 21

The results shown in Table 3 and Table 4 were obtained by following the procedure of Example 10 while using 40.9 g (0.2 mol) of 2-ethylhexyl 2-mercaptoacetate and 6.0 g (0.1 mol) of ethylene sulfide as the raw materials and 0.23 g of tetramethyl ammonium acetate as the catalyst instead.

EXAMPLE 22

The results shown in Table 3 and Table 4 were obtained by following the procedure of Example 10 while using 52.1 g (0.2 mol) of n-dodecyl 2-mercaptoacetate and 6.0 g (0.1 mol) of ethylene sulfide as the raw materials and 0.35 g of tetrabutyl ammonium hydrosulfide as the catalyst instead.

EXAMPLE 23

The results shown in Table 3 and Table 4 were obtained by following the procedure of Example 10 while using 11.0 g (0.1 mol) of thiophenol and 7.4 g (0.1 mol) of propylene sulfide as the raw materials and 0.06 g of tetrabutyl ammonium acetate as the catalyst instead.

EXAMPLE 24

The results shown in Table 3 and Table 4 were obtained by following the procedure of Example 10 while using 46.1 g (0.5 mol) of 1-methyl-2-mercaptoethanol and 7.4 g (0.1 mol) of propylene sulfide as the raw materials and 0.05 g of tetrabutyl ammonium acetate as the catalyst instead.

EXAMPLE 25

The results shown in Table 3 and Table 4 were obtained by following the procedure of Example 10 while using 36.6 g (0.25 mol) of 1-octane thiol and 3.7 g (0.05 mol) of propylene sulfide as the raw materials and 0.12 g of tetrabutyl ammonium acetate as the catalyst instead.

EXAMPLE 26

The results shown in Table 3 and Table 4 were obtained by following the procedure of Example 10 while using 6.9 g (0.05 mol) of thiobenzoic acid and 3.7 g (0.05 mol) of propylene sulfide as the raw materials, 30 g of 1,4-dioxane as the solvent, and 0.08 g of tetrabutyl ammonium acetate as the catalyst instead.

Control 2

The results shown in Table 5 and Table 6 were obtained by following the procedure of Example 10 while using 0.20

TABLE 3

| | Thiol Compound (A) | Alkylene Sulfide (B) | Molar ratio of raw materials (A)/(B) | Catalyst | Amount of catalyst added (wt %) |
|---|---|---|---|---|---|
| Example 10 | Methyl 3-mercaptopropionate | Ethylene sulfide | 5/1 | Tetrabutyl ammonium acetate | 0.3 |
| Example 11 | Methyl 3-mercaptopropionate | Ethylene sulfide | 5/1 | Tetramethyl ammonium acetate | 0.3 |
| Example 12 | Methyl 3-mercaptopropionate | Ethylene sulfide | 5/1 | Tetrabutyl ammonium benzoate | 0.9 |
| Example 13 | Methyl 3-mercaptopropionate | Ethylene sulfide | 5/1 | Tetrabutyl ammonium hydrosulfide | 0.3 |
| Example 14 | Methyl 3-mercaptopropionate | Ethylene sulfide | 5/1 | Tetrabutyl ammonium thiocyanate | 0.3 |
| Example 15 | Methyl 3-mercaptopropionate | Ethylene sulfide | 5/1 | Benzyl trimethyl ammonium hydroxide | 0.08 |
| Example 16 | Methyl 3-mercaptopropionate | Ethylene sulfide | 5/1 | Tetrabutyl ammonium hydroxide | 0.08 |
| Example 17 | Methyl 3-mercaptopropionate | Ethylene sulfide | 5/1 | Tetramethyl ammonium hydroxide | 0.08 |
| Example 18 | Methyl 3-mercaptopropionate | Ethylene sulfide | 5/1 | Triethylmethyl ammonium methyl carbonate | 0.3 |
| Example 19 | Methyl 3-mercaptopropionate | Ethylene sulfide | 5/1 | Tetrabutyl ammonium methoxide | 0.08 |
| Example 20 | Methyl 3-mercaptopropionate | Ethylene sulfide | 5/1 | Cetyl pyridinium methoxide | 0.08 |
| Example 21 | 2-Ethylhexyl 2-mercaptoacetate | Ethylene sulfide | 2/1 | Tetramethyl ammonium acetate | 0.5 |
| Example 22 | n-Dodecyl 2-mercaptoacetate | Ethylene sulfide | 2/1 | Tetrabutyl ammonium hydrosulfide | 0.6 |
| Example 23 | Thiophenol | Propylene sulfide | 1/1 | Tetrabutyl ammonium acetate | 0.3 |
| Example 24 | 1-Methyl-2-mercaptoethanol | Propylene sulfide | 5/1 | Tetrabutyl ammonium acetate | 0.1 |
| Example 25 | 1-Octane thiol | Propylene sulfide | 5/1 | Tetrabutyl ammonium acetate | 0.3 |
| Example 26 | Thiobenzoic acid | Propylene sulfide | 1/1 | Tetrabutyl ammonium acetate | 0.2 |

Note)
The amount of the catalyst added is represented as a concentration (% by weight) in the reaction mixture.
The yield of the product is represented on the basis of the alkylene sulfide.

TABLE 4

| | Total yield of product (%) | Ratio of product | | |
|---|---|---|---|---|
| | | 1 mol adduct | 2 mol adduct | 3 mol adduct |
| Example 10 | 98 | 87 | 13 | 0 |
| Example 11 | 94 | 86 | 14 | Trace amount |
| Example 12 | 92 | 82 | 17 | 1 |
| Example 13 | 96 | 80 | 19 | 1 |
| Example 14 | 95 | 88 | 12 | 0 |
| Example 15 | 98 | 86 | 14 | 0 |
| Example 16 | 98 | 86 | 14 | 0 |
| Example 17 | 97 | 87 | 13 | 0 |
| Example 18 | 80 | 83 | 17 | 0 |
| Example 19 | 95 | 85 | 15 | Trace amount |
| Example 20 | 83 | 87 | 13 | 0 |
| Example 21 | 96 | 99 | 1 | 0 |
| Example 22 | 90 | 98 | 2 | 0 |
| Example 23 | 92 | 99 | 1 | 0 |
| Example 24 | 96 | 97 | 3 | Trace amount |
| Example 25 | 79 | 74 | 22 | 4 |
| Example 26 | 84 | 94 | 6 | 0 | g of benzyl trimethyl ammonium chloride (produced by Wako Pure Chemical Industries Ltd.) as the catalyst instead.

Control 3

The results shown in Table 5 and Table 6 were obtained by following the procedure of Example 10 while using 0.20 g of tetrabutyl ammonium chloride (produced by Wako Pure Chemical Industries Ltd.) as the catalyst instead.

Control 4

The results shown in Table 5 and Table 6 were obtained by following the procedure of Example 10 while using 0.20 g of tetrabutyl ammonium bromide (produced by Wako Pure Chemical Industries Ltd.) as the catalyst instead.

Control 5

The results shown in Table 5 and Table 6 were obtained by following the procedure of Example 10 while using 0.20 g of tetrabutyl ammonium fluoride trihydrate (produced by Wako Pure Chemical Industries Ltd.) as the catalyst instead. In this reaction, a polymer of ethylene sulfide in the form of a white precipitate was partly formed.

Control 6

The results shown in Table 5 and Table 6 were obtained by following the procedure of Example 10 while using 0.20 g of tetrabutyl ammonium iodide (produced by Wako Pure Chemical Industries Ltd.) as the catalyst instead.

TABLE 5

| | Thiol Compound (A) | Alkylene Sulfide (B) | Molar ratio of raw materials (A)/(B) | Catalyst | Amount of catalyst added (wt %) |
|---|---|---|---|---|---|
| Control 1 | Methyl 3-mercaptopropionate | Ethylene sulfide | 5/1 | Benzyl trimethyl ammonium chloride | 0.3 |
| Control 2 | Methyl 3-mercaptopropionate | Ethylene sulfide | 5/1 | Tetrabutyl ammonium chloride | 0.3 |
| Control 3 | Methyl 3-mercaptopropionate | Ethylene sulfide | 5/1 | Tetrabutyl ammonium bromide | 0.3 |
| Control 4 | Methyl 3-mercaptopropionate | Ethylene sulfide | 5/1 | Tetrabutyl ammonium fluoride | 0.3 |
| Control 5 | Methyl 3-mercaptopropionate | Ethylene sulfide | 5/1 | Tetrabutyl ammonium iodide | 0.3 |

Note)
The amount of the catalyst added is represented as a concentration (% by weight) in the reaction mixture.
The yield of the product is represented on the basis of the standards of alkylene sulfide.

TABLE 6

| | Total yield of product (%) | Ratio of product | | |
|---|---|---|---|---|
| | | 1 mol adduct | 2 mol adduct | 3 mol adduct |
| Control 2 | 1 | 100 | 0 | 0 |
| Control 3 | 2 | 100 | 0 | 0 |
| Control 4 | 0 | — | — | — |
| Control 5 | 64 | 79 | 20 | 1 |
| Control 6 | 1 | 100 | 0 | 0 |

EXAMPLE 27

In a four-neck flask provided with a stirrer, a reflux condenser, a thermometer, and a dropping funnel, 60.1 g (0.5 mol) of methyl 3-mercaptopropionate and 0.20 g of tetrabutyl ammonium acetate (produced by Aldrich) were placed and kept under a stream of nitrogen at a temperature of 50° C. and 6.0 g (0.1 mol) of ethylene sulfide was added dropwise thereto over a period of 30 minutes. The ensuing reaction was further continued at the same temperature for three hours. Then, the reaction product was extracted from the flask and analyzed by gas chromatography. It was consequently found to consist of an 1-mol adduct and a 2-mol adduct of ethylene sulfide at a ratio of 87:13 (area ratio of gas chromatograph). The total yield of the obtained ethylene sulfide adducts was 98%, based on the weight of the ethylene sulfide. The results are shown in Table 7 and Table 8.

EXAMPLE 28

The results shown in Table 7 and Table 8 were obtained by following the procedure of Example 27 while using 0.20 g of tetramethyl ammonium acetate (produced by Aldrich) as the catalyst instead.

EXAMPLE 29

The results shown in Table 7 and Table 8 were obtained by following the procedure of Example 27 while using 0.59 g of tetrabutyl ammonium benzoate (produced by Fluka) as the catalyst instead.

EXAMPLE 30

The results shown in Table 7 and Table 8 were obtained by following the procedure of Example 27 while using 0.20 g of tetrabutyl ammonium hydrosulfide (produced by Fluka) as the catalyst instead.

EXAMPLE 31

The results shown in Table 7 and Table 8 were obtained by following the procedure of Example 27 while using 0.13 g of a methanol 40% benzyl trimethyl ammonium hydroxide solution (produced by Tokyo Kasei Kogyo K. K.) as the catalyst instead.

EXAMPLE 32

The results shown in Table 7 and Table 8 were obtained by following the procedure of Example 27 while using 0.53 g of a methanol 10% tetrabutyl ammonium hydroxide solution (produced by Tokyo Kasei Kogyo K. K.) as the catalyst instead.

EXAMPLE 33

The results shown in Table 7 and Table 8 were obtained by following the procedure of Example 27 while using 0.53 g of a methanol 10% tetramethyl ammonium hydroxide solution (produced by Tokyo Kasei Kogyo K. K.) as the catalyst instead.

EXAMPLE 34

A solution of 5.56 g (0.02 mol) of tetrabutyl ammonium chloride in 49.0 g of methanol was kept stirred and 1.08 g (0.02 mol) of sodium methoxide was added gradually thereto. The ensuant reaction was further continued at room temperature for 15 hours. The resultant reaction solution was filtered. The results shown in Table 7 and Table 8 were obtained by following the procedure of Example 27 while using 0.53 g of a methanol 10% solution of tetrabutyl ammonium methoxide thus obtained as the catalyst.

EXAMPLE 35

A solution of 7.16 g (0.20 mol) of cetyl pyridinium chloride monohydrate in 60.4 g of methanol was kept stirred and 1.08 g (0.02 mol) of sodium methoxide was added little by little thereto. The ensuant reaction was further continued at room temperature for 15 hours. The resultant reaction solution was filtered. The results shown in Table 7 and Table 8 were obtained by following the procedure of Example 27 while using 0.53 g of a methanol 10% solution of cetyl pyridinium methoxide thus obtained as the catalyst.

EXAMPLE 36

The results shown in Table 7 and Table 8 were obtained by following the procedure of Example 27 while using 0.13 g of sodium methoxide as the catalyst instead.

EXAMPLE 37

The results shown in Table 7 and Table 8 were obtained by following the procedure of Example 27 while using 0.02 g of potassium hydroxide as the catalyst instead.

EXAMPLE 38

The results shown in Table 7 and Table 8 were obtained by following the procedure of Example 27 while using 0.53 g of N,N,N',N'-tetramethyl ethylene diamine as the catalyst instead.

EXAMPLE 39

The results shown in Table 7 and Table 8 were obtained by following the procedure of Example 27 while using 0.53 g of 2,4,6-tris(dimethylaminomethyl) phenol as the catalyst instead.

EXAMPLE 40

The results shown in Table 7 and Table 8 were obtained by following the procedure of Example 27 while using 0.53 g of N-methyl morpholine as the catalyst instead.

EXAMPLE 41

The results shown in Table 7 and Table 8 were obtained by following the procedure of Example 27 while using 0.53 g of 1,4-diazabicyclo[2.2.2]octane as the catalyst instead.

EXAMPLE 42

The results shown in Table 7 and Table 8 were obtained by following the procedure of Example 27 while using 0.53 g of 1-methyl imidazole as the catalyst instead.

TABLE 8

| | Total yield of product (%) | Ratio of product | | |
|---|---|---|---|---|
| | | 1 mol adduct | 2 mol adduct | 3 mol adduct |
| Example 27 | 98 | 87 | 13 | 0 |
| Example 28 | 94 | 86 | 14 | Trace amount |
| Example 29 | 92 | 82 | 17 | 1 |
| Example 30 | 96 | 80 | 19 | 1 |
| Example 31 | 98 | 86 | 14 | 0 |
| Example 32 | 98 | 86 | 14 | 0 |
| Example 33 | 97 | 87 | 13 | 0 |
| Example 34 | 95 | 85 | 15 | Trace amount |
| Example 35 | 83 | 87 | 13 | 0 |
| Example 36 | 93 | 91 | 9 | 0 |
| Example 37 | 96 | 91 | 9 | 0 |
| Example 38 | 94 | 90 | 10 | 0 |
| Example 39 | 88 | 93 | 7 | 0 |
| Example 40 | 72 | 90 | 10 | 0 |
| Example 41 | 91 | 91 | 9 | 0 |
| Example 42 | 89 | 88 | 12 | 0 |

EXAMPLE 43

The results shown in Table 9 and Table 10 were obtained by following the procedure of Example 27 while using 0.53 g of 4-dimethyl amino pyridine as the catalyst instead.

EXAMPLE 44

The results shown in Table 9 and Table 10 were obtained by following the procedure of Example 27 while using 6.6 g of pyridine as the catalyst instead.

TABLE 7

| | Mercaptocarboxylic ester (A) | Alkylene Sulfide (B) | Molar ratio of raw materials (A)/(B) | Catalyst | Amount of catalyst added (wt %) |
|---|---|---|---|---|---|
| Example 27 | Methyl 3-mercaptopropionate | ES | 5/1 | Tetrabutyl ammonium acetate | 0.3 |
| Example 28 | Methyl 3-mercaptopropionate | ES | 5/1 | Tetramethyl ammonium acetate | 0.3 |
| Example 29 | Methyl 3-mercaptopropionate | ES | 5/1 | Tetrabutyl ammonium benzoate | 0.9 |
| Example 30 | Methyl 3-mercaptopropionate | ES | 5/1 | Tetrabutyl ammonium hydrosulfide | 0.3 |
| Example 31 | Methyl 3-mercaptopropionate | ES | 5/1 | Benzyl trimethyl ammonium hydroxide | 0.08 |
| Example 32 | Methyl 3-mercaptopropionate | ES | 5/1 | Tetrabutyl ammonium hydroxide | 0.08 |
| Example 33 | Methyl 3-mercaptopropionate | ES | 5/1 | Tetramethyl ammonium hydroxide | 0.08 |
| Example 34 | Methyl 3-mercaptopropionate | ES | 5/1 | Tetrabutyl ammonium hydroxide | 0.08 |
| Example 35 | Methyl 3-mercaptopropionate | ES | 5/1 | Cetyl pyridinium methoxide | 0.08 |
| Example 36 | Methyl 3-mercaptopropionate | ES | 5/1 | Sodium methoxide | 0.2 |
| Example 37 | Methyl 3-mercaptopropionate | ES | 5/1 | Potassium hydroxide | 0.3 |
| Example 38 | Methyl 3-mercaptopropionate | ES | 5/1 | N,N,N',N'-Tetramethyl ethylenediamine | 0.8 |
| Example 39 | Methyl 3-mercaptopropionate | ES | 5/1 | 2,4,6-Tris(dimethylaminomethyl)phenol | 0.8 |
| Example 40 | Methyl 3-mercaptopropionate | ES | 5/1 | N-Methyl morpholine | 0.8 |
| Example 41 | Methyl 3-mercaptopropionate | ES | 5/1 | 1,4-Diazabicyclo[2.2.2]octane | 0.8 |
| Example 42 | Methyl 3-mercaptopropionate | ES | 5/1 | 1-Methyl imidazole | 0.8 |

Note)
The amount of the catalyst added is represented as a concentration (% by weight) in the reaction mixture.
The yield of the product is represented on the basis of the alkylene sulfide.
Abbreviation)
ES: Ethylene sulfide;
PS: Propylene sulfide;
Amberlyst A-21: Ion-exchange resin having a tertiary amino group as a functional group (produced by Rohm and Haas Company) was used after washed with water and dried.
Amberlite IRA-904: Ion-exchange resin having a quaternary ammonium group as a functional group (produced by Rohm and Haas Company) was used after pretreated with an aqueous sodium hydroxide solution, washed with water and dried.

EXAMPLE 45

The results shown in Table 9 and Table 10 were obtained by following the procedure of Example 27 while using 6.6 g of 3-picoline as the catalyst instead.

EXAMPLE 46

The results shown in Table 9 and Table 10 were obtained by following the procedure of Example 27 while using 0.20 g of tri-n-butyl phosphine as the catalyst instead.

EXAMPLE 47

The results shown in Table 9 and Table 10 were obtained by following the procedure of Example 27 while using 0.20 g of triphenyl phosphine as the catalyst instead.

EXAMPLE 48

The results shown in Table 9 and Table 10 were obtained by following the procedure of Example 27 while using 21.2 g (0.2 mol) of methyl 2-mercaptoacetate and 6.0 g (0.1 mol) of ethylene sulfide as the raw materials and 0.41 g of 2,4,6-tris (dimethylaminomethyl) phenol as the catalyst instead.

EXAMPLE 49

The results shown in Table 9 and Table 10 were obtained by following the procedure of Example 27 while using 21.2 g (0.2 mol) of methyl 2-mercaptoacetate and 6.0 g (0.1 mol) of ethylene sulfide as the raw materials and 0.16 g of calcium hydroxide as the catalyst instead.

EXAMPLE 50

The results shown in Table 9 and Table 10 were obtained by following the procedure of Example 27 while using 21.2 g (0.2 mol) of methyl 2-mercaptoacetate and 6.0 g (0.1 mol) of ethylene sulfide as the raw materials and 0.16 g of calcium oxide as the catalyst instead.

EXAMPLE 51

The results shown in Table 9 and Table 10 were obtained by following the procedure of Example 27 while using 20.4 g (0.1 mol) of 2-ethylhexyl 2-mercaptoacetate and 7.4 g (0.1 mol) of propylene sulfide as the raw materials, 40 g of tetrahydrofuran as the solvent, and 2.0 g of magnesium oxide as the catalyst instead.

EXAMPLE 52

The results shown in Table 9 and Table 10 were obtained by following the procedure of Example 27 while using 40.9 g (0.2 mol) of 2-ethylhexyl 2-mercaptoacetate and 6.0 g (0.1 mol) of ethylene sulfide as the raw materials and 0.23 g of tetramethyl ammonium acetate as the catalyst instead.

EXAMPLE 53

The results shown in Table 9 and Table 10 were obtained by following the procedure of Example 27 while using 52.1 g (0.2 mol) of n-dodecyl 2-mercaptoacetate and 6.0 g (0.1 mol) of ethylene sulfide as the raw materials and 0.35 g of tetrabutyl ammonium hydrosulfide as the catalyst instead.

EXAMPLE 54

The results shown in Table 9 and Table 10 were obtained by following the procedure of Example 27 while using 10.6 g (0.1 mol) of methyl 2-mercaptoacetate and 6.0 g (0.1 mol) of ethylene sulfide as the raw materials, 30 g of 1,4-dioxane as the solvent, and 0.47 g of triethyl amine as the catalyst instead and changing the reaction time to 10 hours.

EXAMPLE 55

The results shown in Table 9 and Table 10 were obtained by following the procedure of Example 27 while using 10.6 g (0.1 mol) of methyl 2-mercaptoacetate and 7.4 g (0.1 mol) of propylene sulfide as the raw materials, 60 g of methanol as the solvent, and 0.15 g of sodium hydroxide as the catalyst instead and changing the reaction time to 5 hours.

EXAMPLE 56

In the same apparatus as used in Example 27, 24.0 g (0.2 mol) of methyl 3-mercaptopropionate, 40 g of toluene, and 0.4 g of a basic ion-exchange resin (produced by Rohm and Haas Company and marketed under trademark designation of "Amberlyst A-21") were placed and kept under a stream of nitrogen at a temperature of 50° C. and 2.4 g (0.04 mol) of ethylene sulfide was added dropwise thereto over a period of 30 minutes. The ensuant reaction was further continued at the same temperature for two hours. Then, the reaction product was extracted from the apparatus and analyzed by gas chromatography. The results by the analysis were shown in Table 9 and Table 10.

EXAMPLE 57

The results shown in Table 9 and Table 10 were obtained by following the procedure of Example 56 while using 24.0 g (0.2 mol) of ethyl 2-mercaptoacetate and 12.0 g (0.2 mol) of ethylene sulfide as the raw materials instead.

EXAMPLE 58

The results shown in Table 9 and Table 10 were obtained by following the procedure of Example 56 while using 24.0 g (0.2 mol) of methyl 3-mercaptopropionate and 14.8 g (0.2 mol) of propylene sulfide as the raw materials instead.

EXAMPLE 59

The results shown in Table 9 and Table 10 were obtained by following the procedure of Example 56 while using 0.4 g of a basic ion-exchange resin (produced by Rohm and Haas Company and marketed under trademark designation of "Amberlite IRA-904") as the catalyst instead.

TABLE 9

| | Mercaptocarboxylic ester (A) | Alkylene Sulfide (B) | Molar ratio of raw materials (A)/(B) | Catalyst | Amount of catalyst added (wt %) |
|---|---|---|---|---|---|
| Example 43 | Methyl 3-mercaptopropionate | ES | 5/1 | 4-Dimethyl amino pyridine | 0.8 |
| Example 44 | Methyl 3-mercaptopropionate | ES | 5/1 | Pyridine | 10 |
| Example 45 | Methyl 3-mercaptopropionate | ES | 5/1 | 3-Picoline | 10 |
| Example 46 | Methyl 3-mercaptopropionate | ES | 5/1 | Tri-n-butyl phosphine | 0.3 |
| Example 47 | Methyl 3-mercaptopropionate | ES | 5/1 | Triphenyl phosphine | 0.3 |
| Example 48 | Methyl 2-mercaptoacetate | ES | 2/1 | 2,4,6-Tris(dimethylaminomethyl)phenol | 1.5 |
| Example 49 | Methyl 2-mercaptoacetate | ES | 2/1 | Calcium hydroxide | 0.6 |
| Example 50 | Methyl 2-mercaptoacetate | ES | 2/1 | Calcium oxide | 0.6 |
| Example 51 | 2-Ethylhexyl 2-mercaptoacetate | PS | 1/1 | Magnesium oxide | 2.9 |
| Example 52 | 2-Ethylhexyl 2-mercaptoacetate | ES | 2/1 | Tetramethyl ammonium acetate | 0.5 |
| Example 53 | n-Dodecyl 2-mercaptoacetate | ES | 2/1 | Tetrabutyl ammonium hydrosulfide | 0.6 |
| Example 54 | Methyl 2-mercaptoacetate | ES | 1/1 | Triethyl amine | 1.0 |
| Example 55 | Methyl 2-mercaptoacetate | PS | 1/1 | Sodium hydroxide | 0.2 |
| Example 56 | Methyl 3-mercaptopropionate | ES | 5/1 | Amberlyst A-21 | 0.6 |
| Example 57 | Ethyl 2-mercaptoacetate | ES | 1/1 | Amberlyst A-21 | 0.5 |
| Example 58 | Methyl 3-mercaptopropionate | PS | 1/1 | Amberlyst A-21 | 0.5 |
| Example 59 | Methyl 3-mercaptopropionate | ES | 5/1 | Amberlite IRA-904 | 0.6 |

Note)
The amount of the catalyst added is represented as a concentration (% by weight) in the reaction mixture.
The yield of the product is represented on the basis of the alkylene sulfide.
Abbreviation)
ES: Ethylene sulfide;
PS: Propylene sulfide;
Amberlyst A-21: Ion-exchange resin having a tertiary amino group as a functional group (produced by Rohm and Haas Company) was used after washed with water and dried.
Amberlite IRA-904: Ion-exchange resin having a quaternary ammonium group as a functional group (produced by Rohm and Haas Company) was used after pretreated with an aqueous sodium hydroxide solution, washed with water and dried.

TABLE 10

| | Total yield of product (%) | Ratio of product | | |
|---|---|---|---|---|
| | | 1 mol adduct | 2 mol adduct | 3 mol adduct |
| Example 43 | 91 | 87 | 13 | Trace amount |
| Example 44 | 98 | 87 | 13 | 0 |
| Example 45 | 96 | 86 | 14 | Trace amount |
| Example 46 | 85 | 87 | 13 | 0 |
| Example 47 | 94 | 88 | 11 | 1 |
| Example 48 | 85 | 99 | 1 | 0 |
| Example 49 | 94 | 97 | 3 | 0 |
| Example 50 | 80 | 97 | 3 | 0 |
| Example 51 | 72 | 89 | 11 | 0 |
| Example 52 | 96 | 99 | 1 | 0 |
| Example 53 | 90 | 98 | 2 | 0 |
| Example 54 | 91 | 88 | 7 | 5 |
| Example 55 | 93 | 95 | 5 | 0 |
| Example 56 | 98 | 89 | 11 | Trace amount |
| Example 57 | 98 | 99 | 1 | 0 |
| Example 58 | 73 | 88 | 12 | 0 |
| Example 59 | 87 | 85 | 15 | Trace amount |

The entire disclosure of Japanese Patent Application Nos. 08-186372i 08-186373 and 08-186374 filed on Jul. 16, 1996 including specification, claims and summary are incorporated herein by reference in its entirety.

What is claimed is:

1. A method for the production of a sulfide group-containing mercaptocarboxylic ester represented by the general formula (7):

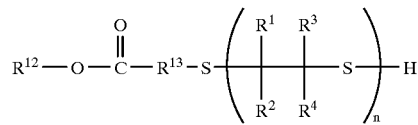

(wherein $R^1$, $R^2$, $R^3$, and $R^4$, which may be identical or different, each represents a hydrogen atom, an alkyl group of 1 to 10 carbon atoms, or an aromatic group of 6 to 15 carbon atoms, $R^{12}$ for a hydrocarbon group of 1 to 20 carbon atoms, and $R^{13}$ for an alkylene group of 1 to 3 carbon atoms, and n is an integer in the range of 1 to 3), which comprises sequentially adding an alkylene sulfide represented by the general formula (2):

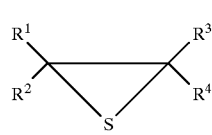

(wherein $R^1$, $R^2$, $R^3$, and $R^4$ have the same meanings as defined above) to react with a mercaptocarboxylic ester represented by the general formula (6):

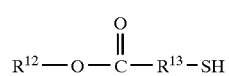

(wherein $R^{12}$ and $R^{13}$ have the same meanings as defined above).

2. A method according to claim 1, wherein the reaction is carried out in the presence of a basic catalyst or a phosphine catalyst.

3. A method according to claim 1, wherein the amount of said mercaptocarboxylic ester is in the range of 1 to 10 mols per mol of the alkylene sulfide.

4. A method according to claim 1, wherein said alkylene sulfide is ethylene sulfide or propylene sulfide and said mercaptocarboxylic ester is 3-mercaptopropionic ester or 2-mercaptoacetic ester.

5. The method of claim 2 wherein the basic catalyst is an ion-exchange resin having a tertiary amino group, a quaternary ammonium group or a pyridine ring.

* * * * *